United States Patent [19]
Gresser et al.

[11] 3,951,740
[45] Apr. 20, 1976

[54] MANUFACTURE OF INTERFERON

[75] Inventors: Ion Gresser; Michael G. Tovey, both of Paris, France

[73] Assignee: Agence Nationale de Valorisation de la Recherche (ANVAR), Neuilly-sur-Seine, France

[22] Filed: Jan. 7, 1975

[21] Appl. No.: 539,176

[30] Foreign Application Priority Data
Jan. 11, 1974 France .................. 74.00949
Aug. 26, 1974 France .................. 74.29144

[52] U.S. Cl. ............................ 195/1.8; 195/29
[51] Int. Cl.² .................................... C12D 13/02
[58] Field of Search .......... 195/28 N, 28 R, 29, 195/1.8; 424/85, 177

[56] References Cited
UNITED STATES PATENTS
3,548,053  12/1970  Joshi et al. .................. 424/85
3,773,924  11/1973  Ho et al. .................... 424/85

OTHER PUBLICATIONS
Nature Vol. 182 pp. 1075–1074 (1958).
J. Gen. Virol. Vol. 15 (Pt. 2) pp. 119–128 (1972).
J. Gen. Virol. Vol. 17, pp. 107–109 (1972).

*Primary Examiner*—Alvin E. Tanenholtz
*Attorney, Agent, or Firm*—Brumbaugh, Graves, Donohue & Raymond

[57] ABSTRACT

This invention relates to the production of interferon. In accordance with the present invention, interferon is produced by growing a continuous cell line in a suspension culture, the cells first being primed by cultivation in the presence of interferon specific to the cells and L-glutamine, interferon production being initiated by contacting the cells with a high concentrated suspension of virus inducer, then removing the virus and incubating the cells in a nutrient medium. Concentration and purification to give interferon preparations can be effected by known methods. Various types of interferon preparations of high titre have been produced on an industrial scale.

9 Claims, No Drawings

MANUFACTURE OF INTERFERON

This invention relates to the production of interferon, and in particular on an industrial scale.

Interferon can be produced by the growth of animal cells in monolayer cultures, and this can be used to produce interferon preparations of high titre. However, monolayer culture techniques do not lend themselves readily to industrial-scale production. They have an inherent limitation since the cells grow on a solid surface, and in order to obtain an adequate oxygenation rate for cell growth, a high ratio of cell surface to medium volume is required. This culture technique also involves a large number of operations requiring very specialised handling, each handling operation involving a risk of contamination.

Animal cells can, however, be grown in virtually unlimited quantities, in stirred suspension culture in a single vessel. Oxygenation, pH, and the introduction of nutrients can be automatically controlled to obtain increased cell populations, and a more efficient utilisation of the nutrient medium, than in the case of monolayer cultures.

For these reasons, attempts have been made in the last few years to produce interferon preparations of high titre in suspension cultures. These attempts were unsuccessful, as the amounts of interferon produced were low, and therefore were not of interest on an industrial scale.

According to the present invention there is provided a process for the preparation of interferon of high titer which comprises growing interferon-producing cells from a continuous cell line in a stirred suspension culture while effecting the following process stages:

a. adding a priming dose of interferon, the interferon being specific to the species from which the cells are derived, to a culture medium of cells grown in suspension up to the saturation density of the cells in the medium, and enough L-glutamine to keep the cells in an active metabolic state, and effecting priming of the cells, with suitable stirring of the medium;

b. stopping the stirring, and separating the cells by sedimentation from the supernatant liquid;

c. resuspending the cells in a small volume of a highly concentrated suspension of a virus inducer, leaving the cells in contact with the virus, and thereafter removing the virus inducer by centrifugation;

d. subjecting the cells to metabolic inhibitors and removing the inhibitors by centrifugation;

e. resuspending the cells in a nutrient medium without serum, in which the cells are incubated; and f. separating the cells by sedimentation, collecting the supernatant liquid containing the interferon, and concentrating and purifying the interferon.

In a preferred embodiment a continuous cell line is grown in a suspension culture in a large culture vessel with stirring until saturation density of the cells in the medium has been reached. Thereafter, a small amount of interferon specific to the cells is added, and the priming stage begins. In addition, L-glutamine is added at the beginning of this stage to maintain the cells in an active metabolic state. The priming will usually be effected for several hours at 37°C. At the end of the priming stage, stirring is stopped so that the cells separate by sedimentation under gravity. The supernatant fluid is sucked off under vacuum. The cell pellet at the bottom of the tank is suspended in a highly concentrated suspension of virus inducer, using as low a volume as possible. Contact with the virus is preferably effected for about 1 hour. After contacting the cells with the virus inducer, the virus is removed by centrifugation, preferably so that it can be recovered and re-used in another operation. The re-suspended cell mass is subjected to the action of metabolic inhibitors for several hours, and after elimination of the inhibitors by centrifugation, the cells are suspended in the nutrient medium without serum. Interferon develops during this stage, which is preferably effected for about 15 to 20 hours.

Separation of the cells is effected by sedimentation under gravity, and the interferon in the supernatant liquid can be concentrated and purified by known methods.

In accordance with the present invention, interferon preparations are produced by a combination of stages, certain of the stages being effected under particular conditions, for example as follows:

the addition of L-glutamine at the start of the priming stage is intended to keep the cells in an active, metabolic state, and it is essential in order to obtain high yields of interferon;

adsorption of the virus inducer on the cells is effected by resuspending the cells in as small a volume as possible of a very concentrated suspension of virus inducer, the cell concentration and the virus concentration both being high in the suspension in order to increase contact between the virus inducer and the cells. This is important in order to obtain interferon titres as high as those obtained in monolayer cultures when using cultivation in suspension. The volume of viral suspension is preferably 0.01 of the original culture volume, and thereby a multiplicity of infection of 1 is obtained. This induction volume is critical. Thus, if it is reduced by one half (that is to say to 0.005 of the original culture volume) it can be difficult to resuspend the cells, and this results in a substantial loss of cells. However, if the induction volume is increased, the quantity of interferon produced can be reduced.

The virus inducer, which is separated by centrifuging the cells after the adsorption stage, can be recovered and often it can be reused more than eight times in subsequent operations, without loss of induction capacity. This represents a substantial economy in virus inducer, when the process is used on an industrial scale.

Finally, separation of the cells by sedimentation under gravity in two stages of the process (i. e. after the priming and incubation stages) makes the process very interesting on an industrial scale, as the processing can be carried out automatically with the aid of mechanical pumps. Thus, highly specialised operatives need not be used to work the process, and it considerably reduces the risks of contamination.

Using the present invention, mouse interferon has been produced from mouse cells transformed by Sarcoma virus, called "C-243-3 cells", and human interferon has been produced from a line of Burkitt cells called "Namalva cells". However, other types of interferon can be produced, for example those specific to the porcine species, to the bovine species, and to the feline species, provided cell lines are available from those species which are able to multiply in suspension culture.

The following examples are given by way of illustration only, and they show the preparation of mouse interferon and human interferon.

EXAMPLE 1

Preparation of mouse interferon from C-243-3 cells

The cell culture was effected in a 20 liter culture tank, with stirring. The speed of stirring was critical, namely at 50 r.p.m. At too high a stirring speed, the cells would be killed by mechanical shearing, and if too slow, the culture would be insufficiently oxygenated.

C-243-3 cells from the mouse were sown at a concentration of $2 \times 10^5$ cells per ml in an Eagle essential minimum medium as modified by Joklik, and supplemented by 10% of calf serum. Cultivation was at 37°C. For optimum growth, the pH was held at 7.2. Under optimum conditions, cell saturation was obtained at a concentration of $1.5 \times 10^6$ cells per ml. This saturation density was reached after 48 hours of growth.

A small, priming amount of mouse interferon was then added, namely 50 units of mouse interferon per ml. L-Glutamine was also added at the rate of 0.5 mg/ml to maintain the cells in an active metabolic state. The priming stage was continued for 18 hrs. at 37°C.

Twelve hours after the start of the priming, stirring was stopped, and the cells were allowed to deposit under gravity for the 6 remaining hours. It was found that 6 hours were necessary to obtain a complete sedimentation of the cells. 90 to 95% of the spent nutrient medium were removed under vacuum. The residual medium, containing the cells, was centrifuged under 2000 g for 10 minutes.

The cell pellet obtained at the bottom of the container was resuspended in a suspension of live virus of the Hertz strain of Newcastle disease, to provide a multiplicity of infection of 1 in a volume equal to 0.01 of the volume of original culture. For example, the cells present in 10 liters of the initial culture liquid were resuspended in 100 ml of the suspension of Newcastle disease virus. This induction volume was critical, and it could not be reduced nor increased without disadvantage.

The suspension of the Newcastle disease virus was prepared by ultra-centrifugation of allantoic liquid, the pellet of virus being suspended in some Eagle minimum medium at the required concentration.

After adsorption for one hour, the cells were deposited by centrifugation for 10 minutes at 2000 g. The virus inducer was recovered and stored at −70°C for reuse. The separated C-243-3 cells were resuspended at a concentration of $10^7$ cells per ml in an Eagle minimum essential medium containing 2% of calf serum. This cell concentration was not critical, and could be increased to $5 \times 10^7$ cells per ml if desired (that is to say 6 liters of cells, at a concentration of $1 \times 10^6$ cells per ml, may be reduced to 1 liter or even 500 ml.).

10 micrograms per ml of cycloheximide are added, and the cells were stirred as previously described for 3 hours, at the end of which 3 micrograms per ml of D-actinomycin were added. After an additional 2 hours, the inhibitors were removed by centrifuging at 2000 g for 10 minutes. It was not necessary to wash the cell pellet.

The cell pellet was resuspended in a volume of nutrient medium, without serum, equal to the original culture volume, and incubated for 18 hours with stirring. During this incubation stage, the stirring was not critical.

The cells were then allowed to deposit under gravity for 6 hours, as after the priming stage.

The supernatant liquid containing the interferon was sucked off, and concentrated by fractionation with ammonium sulphate at pH 2, with 100% recovery. This was accompanied by a substantial purification.

Interferon preparations have been regularly produced with a titre of 128,000 international reference units per ml. In numerous examples, titres of 512,000 units per ml were even obtained, and 20,000 ml of this preparation can be produced in a week by one technician. The interferon preparations can easily be concentrated a hundred times by fractionation with ammonium sulphate, with 100% recovery. In this way, 200 ml of interferon-containing solution can be obtained having a titre of $1.28 \times 10^7$ units per ml, per week.

EXAMPLE 2

Preparation of human interferon from "Namalva"-line of Burkitt cells

A continuous line of human leucocytes, called "Namalva" Burkitt cell line, was used. This line was isolated by Prof. George Klein of the Karolinska Institute in Stockholm from an African suffering from Burkitt's disease. It was selected by Dr. Hans Strander of the same Institute for its high capability for producing interferon.

"Namalva" cells were sown at a concentration of $2 \times 10^5$ cells per ml in a RPMI 1640 nutrient medium (a nutrient medium sold under this name by GIBCO supplemented by 10% of calf foetus serum. The cells were cultivated in suspension in a 20-liter tank at 37°C, with mechanical stirring, until the cell saturation density was obtained. This was $2.5 \times 10^6$ cells/ml. This saturation density was reached after growth for 72 hours.

A priming amount of 10 units of human interferon per ml and 0.5 mg/ml of L-glutamine to keep the cells in an active metabolic state were then added. Priming was continued for 18 hours, at 37°C.

During this stage, the cells were allowed to deposit under gravity, and after 18 hours the supernatant liquid was sucked off. The residual medium containing the cells was centrifuged, and the resulting cell mass was resuspended in 0.01 of the original culture volume of a suspension of virus inducer (live virus, Herz strain, of Newcastle disease) to provide a multiplicity of infection of 1.

After a short adsorption stage, the cells were separated by centrifuging the virus inducer which was recovered. The Burkitt cells were resuspended at a concentration of $10^7$ cells/ml in RPMI 1640 medium, which had been supplemented by 2% of calf foetus serum and contained 10 micrograms per ml of cycloheximide.

After several hours exposure to the cycloheximide, the latter was removed by centrifugation, and the cell mass was resuspended in RPMI 1640 nutrient medium, without serum, at a concentration of $10^7$ cells/ml, and incubated for 18 hours with stirring.

The resulting cells were allowed to deposit under gravity, and the supernatant liquid containing the interferon was sucked off, concentrated, and purified by known methods.

In this way, using "Namalva" cells, human interferon preparations were obtained with a titre of 1/1280. After concentration 100 to 1000 times, an interferon was obtained with a titre of 1 million international reference units per ml on human cells.

In accordance with the present invention, large amounts of human interferon of high titre can be produced on an industrial scale.

Furthermore, large amounts of interferon can be produced for veterinary medicine. This is of particular value as it may enable efficient therapeutic or prophylactic effects to be obtained against a large number of cattle diseases which are detrimental to the economy, such as foot-and-mouth disease and rinderpest.

We claim:

1. A process for the preparation of interferon of high titre which comprises growing interferon-producing cells from a continuous cell line in a stirred suspension culture while effecting the following process stages:
   a. adding a priming dose of interferon, the interferon being specific to the species from which the cells are derived, to a culture medium of cells grown in suspension up to the saturation density of the cells in the medium, and enough L-glutamine to keep the cells in an active metabolic state, and effecting priming of the cells with suitable stirring of the medium;
   b. stopping the stirring and separating the cells by sedimentation from the supernatant liquid;
   c. resuspending the cells in a small volume of a highly concentrated suspension of a virus inducer, leaving the cells in contact with the virus, and thereafter removing the virus inducer by centrifugation;
   d. subjecting the cells to metabolic inhibitors and removing the inhibitors by centrifugation;
   e. resuspending the cells in a nutrient medium without serum, in which the cells are incubated; and
   f. separating the cells by sedimentation, collecting the supernatant liquid containing the interferon, and concentrating and purifying the interferon.

2. A process according to claim 1, wherein during stages (b) and (f), sedimentation of the cells is effected under gravity, and separating the resulting pellet of cells from the supernatant liquid by suction.

3. A process according to claim 1, wherein the resuspension in stage (c) is effected in a volume of virus suspension equal to 0.01 of the volume of the initial culture medium, to produce a multiplicity of infection of 1.

4. A process according to claim 1, wherein the inductor virus which is removed in stage (c) is recovered and reused more than 8 times.

5. A process according to claim 1, wherein mouse specific interferon is prepared from mouse Sarcoma virus transformed C-243-3 cells.

6. A process according to claim 1, wherein human specific interferon is prepared from "Namalva" Burkitt cell line.

7. A process according to claim 5, wherein the culture medium is stirred at a speed of 50 r.p.m. during stage of priming.

8. A process according to claim 6, wherein the culture medium is stirred at a speed of 50 r.p.m. during stage of priming.

9. A process according to claim 1, wherein the virus inducer is Newcastle disease virus.

* * * * *